US00PP19486P2

(12) United States Plant Patent
Klemm

(10) Patent No.: US PP19,486 P2
(45) Date of Patent: Nov. 25, 2008

(54) ***GERANIUM* PLANT NAMED 'KLEPS06126'**

(50) Latin Name: *Pelargonium×hortorum*
Varietal Denomination: KLEPS06126

(75) Inventor: Nils Klemm, Stuttgart (DE)

(73) Assignee: Klemm +Sohn + Co. KG, Stuttgart (DE)

( * ) Notice: Subject to any disclaimer, the term of this patent is extended or adjusted under 35 U.S.C. 154(b) by 0 days.

(21) Appl. No.: 12/002,472

(22) Filed: Dec. 17, 2007

(51) Int. Cl.
*A01H 5/00* (2006.01)

(52) U.S. Cl. ..... Plt./329; Plt./328
(58) Field of Classification Search ..... Plt./329, Plt./328
See application file for complete search history.

(56) References' Cited

PUBLICATIONS

UPOV ROM GTITM Computer Database, GTI Jouve Retrieval Software 2007/05 Citation for 'KLEPS06126'.*

* cited by examiner

*Primary Examiner*—Wendy C. Haas
(74) *Attorney, Agent, or Firm*—C. A. Whealy

(57) ABSTRACT

A new and distinct cultivar of Zonal *Geranium* plant named 'KLEPS06126', characterized by its upright and rounded plant habit; freely branching habit; dark-green colored leaves; freely flowering habit; semi-double dark pink-colored flowers with purple-colored central spots; and good garden performance.

1 Drawing Sheet

Botanical designation: *Pelargonium×hortorum*.
Cultivar denomination: 'KLEPS06126'.

BACKGROUND OF THE INVENTION

The present invention relates to a new and distinct cultivar of Zonal *Geranium*, botanically known as *Pelargonium× hortorum,* and hereinafter referred to by the name 'KLEPS06126'.

The new Zonal *Geranium* is a product of a planned breeding program conducted by the Inventor in Stuttgart, Germany. The objective of the breeding program is to create new freely-branching and uniform Zonal *Geranium* cultivars with early flowering habit and attractive foliage and flower coloration.

The new Zonal *Geranium* originated from a cross-pollination made by the Inventor in Stuttgart, Germany in August, 2002 of the *Pelargonium×hortorum* cultivar Klecona, disclosed in U.S. Plant patent application Ser. No. 09/250,015, now abandoned, as the female, or seed, parent with a proprietary selection of *Pelargonium×hortorum* identified as code number Z 21 182, not patented, as the male, or pollen, parent. The cultivar KLEPS06126 was discovered and selected by the Inventors as a flowering plant from within the progeny of the stated cross-pollination in a controlled environment in Stuttgart, Germany in June, 2003.

Asexual reproduction of the new Zonal *Geranium* by vegetative terminal cuttings in a controlled environment in Stuttgart, Germany since September, 2003, has shown that the unique features of this new Zonal *Geranium* are stable and reproduced true to type in successive generations.

SUMMARY OF THE INVENTION

The cultivar KLEPS06126 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLEPS06126'. These characteristics in combination distinguish 'KLEPS06126' as a new and distinct cultivar of Zonal *Geranium:*

1. Upright and rounded plant habit.
2. Freely branching habit.
3. Dark-green colored leaves.
4. Freely flowering habit.
5. Semi-double dark pink-colored flowers with purple-colored central spots.
6. Good garden performance.

Plants of the new Zonal *Geranium* differ primarily from plants of the female parent, the cultivar Klecona, in the following characteristics:

1. Plants of the new *Geranium* are more compact than plants of the cultivar Klecona.
2. Leaves of plants of the new *Geranium* are darker green in color than leaves of plants of the cultivar Klecona.
3. Plants of the new *Geranium* and the cultivar Klecona differ in flower color as plants of the cultivar Klecona have red purple-colored flowers.

Plants of the new Zonal *Geranium* differ primarily from plants of the male parent selection in the following characteristics:

1. Plants of the new *Geranium* are more compact than and not as vigorous as plants of the male parent selection.
2. Leaves of plants of the new *Geranium* are darker green in color than leaves of plants of the male parent selection.
3. Plants of the new *Geranium* and the male parent selection differ in flower color as plants of the male parent selection have lavender-colored flowers.

Plants of the new Zonal *Geranium* can be compared to plants of the *Pelargonium×hortorum* cultivar 'Moonlight Kitty', not patented. In side-by-side comparisons conducted in Stuttgart, Germany, plants of the new Zonal *Geranium* differed from plants of the cultivar Moonlight Kitty in the following characteristics:

1. Plants of the new Zonal *Geranium* were larger than plants of the cultivar Moonlight Kitty.
2. Plants of the new Zonal *Geranium flowered later than plants of the cultivar Moonlight Kitty.*
3. Plants of the new Zonal *Geranium* and the cultivar Moonlight Kitty differed in flower color as plants of the cultivar Moonlight Kitty had lavender-colored flowers.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*. The photograph comprises a side perspective view of a typical flowering plant of 'KLEPS06126' grown in a container.

DETAILED BOTANICAL DESCRIPTION

The photographs and following observations, measurements and values describe plants grown in Stuttgart, Germany in a glass-covered greenhouse during the spring and under conditions which closely approximate commercial *Geranium* production. During the production of the plants, day temperatures ranged from 16° C. to 23° C., night temperatures ranged from 8° C. to 16° C. and light levels ranged from 20,000 lux to 55,000 lux. Plants were about three months old when the photograph and the description were taken. In the detailed description, color references are made to The Royal Horticultural Society Colour Chart, 1995 Edition, except where general terms of ordinary dictionary significance are used.

Botanical Classification: *Pelargonium×hortorum* cultivar KLEPS06126.

Parentage:

*Female, or seed, parent.*—*Pelargonium×hortorum* cultivar Klecona, disclosed in U.S. Plants patent application Ser. No. 09/250,015.

*Male or pollen parent.*—Proprietary selection of *Pelargonium×hortorum* identified as code number Z 21 128, not patented.

Propagation:

*Type.*—By vegetative terminal cuttings.

*Time to initiate roots, summer.*—About six days at temperatures of 22° C.

*Time to initiate roots, winter.*—About eight days at temperatures of 20° C.

*Time to produce a rooted young plant, summer.*—About 18 days at temperatures of 22° C.

*Time to produce a rooted young plant, winter.*—About 20 days at temperatures of 20° C.

*Root description.*—Thick, fibrous; white in color.

*Rooting habit.*—Freely branching, moderately dense.

Plant Description:

*Plant/growth habit.*—Upright to rounded plant habit; densely foliated. Moderately vigorous growth habit. Freely basal branching habit with about four to five lateral branches per plant.

*Plant height, to top of umbels.*—About 22 cm to 25 cm.

*Plant height, to top of leaves.*—About 15 cm to 18 cm.

*Plant width.*—About 22 cm to 24 cm.

*Lateral branches.*—Length: About 6 cm. Internode length: About 0.5 cm to 1 cm. Texture: Pubescent. Color: 137B overlain with 178A.

Foliage description:

*Arrangement.*—Alternate; simple.

*Length.*—About 3 cm to 6 cm.

*Width.*—About 5 cm to 8 cm.

*Shape.*—Reniform.

*Apex.*—Rounded.

*Base.*—Cordate.

*Margin.*—Crenate.

*Venation pattern.*—Palmate.

*Texture, upper surface.*—Glabrous, rough.

*Texture, lower surface.*—Pubescent; rough.

*Color.*—Developing and fully expanded foliage, upper surface: 137B; venation, 137C. Developing and fully expanded foliage, lower surface: 137C; venation, 137C. Zonation pattern: Not observed.

*Petiole.*—Length: About 4 cm to 6 cm. Diameter: About 2.5 mm. Texture, upper and lower surfaces: Rough. Color, upper and lower surfaces: 137B overlain with 178B.

Flower description:

*Flower arrangement.*—Semi-double rotate flowers arranged in rounded hemispherical umbels arising from apical leaf axils. Umbels displayed above the foliage on strong peduncles. Flowers face upright to outward; flowers slightly cupped. Flowers not persistent. Flowers not fragrant.

*Quantity of flowers.*—Freely flowering habit; about 20 to 28 flower buds and open flowers per umbel; about eight to nine umbels per plant.

*Flowering season.*—Year-round under greenhouse conditions. In the garden in Stuttgart, Germany, flowering is continuous from spring until frost in autumn.

*Flower longevity.*—Individual flowers last about six to ten days on the plant.

*Umbel height.*—About 8 cm.

*Umbel diameter.*—About 8 cm to 12 cm.

*Flower diameter.*—About 4 cm.

*Flower depth (height).*—About 1 cm to 2 cm.

*Flower buds.*—Length: About 1 cm to 1.3 cm. Diameter: About 5 mm to 8 mm. Shape: Elliptic. Color: 137B overlain with 178B.

*Petal.*—Quantity per flower: About six to eight. Length: About 2.5 cm. Width: About 2 cm. Shape: Ovate. Apex: Rounded. Base: Attenuate. Margin: Entire. Texture, upper and lower surfaces: Smooth, glabrous; satiny to velvety. Color: When opening and fully opened, upper surface: 80D; spot, close to 66A; venation, 80C; color becoming closer to 80C with development. When opening and fully opened, lower surface: 75C; venation, 80C.

*Petaloids.*—Quantity per flower: About one to three. Length: About 2 mm to 10 mm. Width: About 1 mm to 5 mm. Shape: Irregularly-shaped. Apex: Rounded. Base: Attenuate. Margin: Entire. Texture, upper and lower surfaces: Smooth, glabrous; satiny to velvety. Color: When opening and fully opened, upper surface: 80D; venation, 80C. When opening and fully opened, lower surface: 75C; venation, 80C.

*Sepals*.—Quantity per flower: Five, arranged in a single whorl. Length: About 5 mm to 10 mm. Width: About 4 mm to 7 mm. Shape: Elliptic. Apex: Acute. Base: Attenuate. Margin: Entire. Texture, upper surface: Smooth, glabrous. Texture, lower surface: Pubescent. Color, upper surface: 137C. Color, lower surface: 137B overlain with 178A.

*Peduncle* (*umbel stem*).—Length: About 10 cm to 15 cm. Diameter: About 4 mm to 5 mm. Strength: Strong. Angle: Mostly erect. Texture: Pubescent. Color: 178A. Length: About 1.5 cm to 2 cm. Diameter: About 1 mm to 2 mm. Strength: Moderately strong. Angle: Erect to about 110° C. from vertical. Texture: Pubescent. Color: 178A.

*Reproductive organs*.—Androecium: Stamen quantity per flower: About five. Anther length: About 3 mm. Anther shape: Ovate. Anther color: 55A. Pollen amount: Moderate. Pollen color: 33C. Gynoecium: Pistil quantity per flower: One. Pistil length: About 8 mm. Stigma shape: Tapering; reflexed. Stigma color: 57C. Style length: About 3 mm to 5 mm. Style color: 57D. Ovary color: 149D.

*Seed*.—Seed development has not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind and temperatures ranging from about 6° C. to about 33.5° C. and have demonstrated good garden performance.

It is claimed:

1. A new and distinct Zonal *Geranium* plant named 'KLEPS06126' as illustrated and described.

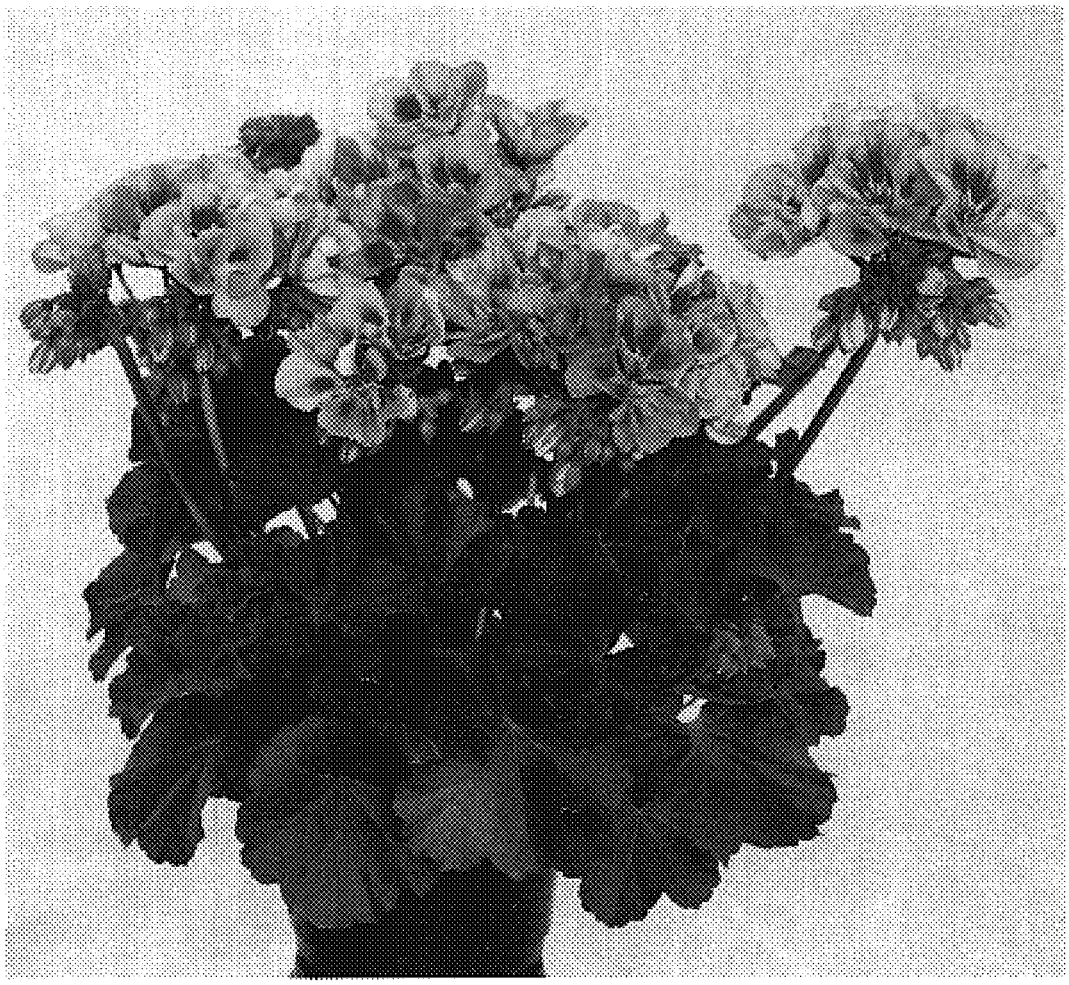

* * * * *